(12) United States Patent
Garabet et al.

(10) Patent No.: US 6,254,619 B1
(45) Date of Patent: Jul. 3, 2001

(54) MICROKERATOME

(76) Inventors: Antoine Garabet, 2220 E. Alosta Ave., Suite 205, Glendora, CA (US) 91740; Yevgeniy Kuklin, 1530 N. Pointsettia Pl., Apt. 340, Los Angeles, CA (US) 90046

( * ) Notice: Subject to any disclaimer, the term of this patent is extended or adjusted under 35 U.S.C. 154(b) by 0 days.

(21) Appl. No.: 09/473,582

(22) Filed: Dec. 28, 1999

(51) Int. Cl.[7] .................................................. A61F 9/00
(52) U.S. Cl. ............................................................ 606/166
(58) Field of Search ............................... 606/4, 161, 166, 606/170, 171, 5; 604/294

(56) References Cited

U.S. PATENT DOCUMENTS

| | | | |
|---|---|---|---|
| 5,133,726 | 7/1992 | Ruiz et al. | 606/166 |
| 5,290,301 | 3/1994 | Lieberman | 606/166 |
| 5,342,378 * | 8/1994 | Giraud et al. | 606/166 |
| 5,441,511 | 8/1995 | Hanna | 606/166 |
| 5,464,417 | 11/1995 | Eick | 606/166 |
| 5,486,188 | 1/1996 | Smith | 606/166 |
| 5,496,339 | 3/1996 | Koepnick | 606/166 |
| 5,586,980 | 12/1996 | Kremer et al. | 606/4 |
| 5,591,174 * | 1/1997 | Clark et al. | 606/130 |
| 5,595,570 | 1/1997 | Smith | 606/166 |
| 5,624,456 | 4/1997 | Hellenkamp | 606/166 |
| 5,653,723 | 8/1997 | Kamerling et al. | 606/166 |
| 5,658,303 | 8/1997 | Koepnick | 606/166 |
| 5,674,233 | 10/1997 | Dybbs | 606/166 |
| 5,690,657 | 11/1997 | Koepnick | 606/166 |
| 5,697,945 | 12/1997 | Kritzinger et al. | 606/161 |
| 5,752,967 | 5/1998 | Kritzinger et al. | 606/166 |
| 5,772,675 | 6/1998 | Hellenkamp | 606/166 |
| 5,779,723 | 7/1998 | Schwind | 606/166 |
| 5,817,115 | 10/1998 | Nigam | 606/166 |
| 5,934,285 | 8/1999 | Kritzinger et al. | 128/898 |
| 5,938,674 | 8/1999 | Terry | 606/166 |
| 5,944,731 | 8/1999 | Hanna | 606/166 |
| 5,947,987 | 9/1999 | Gordon et al. | 606/166 |
| 5,964,776 | 10/1999 | Peyman | 606/166 |
| 5,989,272 * | 11/1999 | Barron et al. | 606/166 |
| 5,997,559 * | 12/1999 | Ziemer | 606/166 |

* cited by examiner

Primary Examiner—Henry J. Recla
Assistant Examiner—Anthony S. King
(74) Attorney, Agent, or Firm—Christie, Parker & Hale, LLP

(57) ABSTRACT

A microkeratome for use with a handpiece and a microkeratome blade, the microkeratome having a positioning assembly and a head portion with a base portion and an insert portion. The positioning assembly has a platform with a corneal opening and a suction ring for application to the surface of the patient's eyeball. The positioned assembly has two spaced apart guide walls that are high enough to prevent a patient's eyelids from passing over the upper surface of the positioning assembly. The base portion has a lower planar face with a base slot extending therethrough through which the microkeratome blade will extend, and opposing sides with skates to slidably engage with inner sliding surfaces of guide walls. The insert portion lockably fits into the base portion. Stops are present to control the amount of uncut corneal flap.

38 Claims, 16 Drawing Sheets

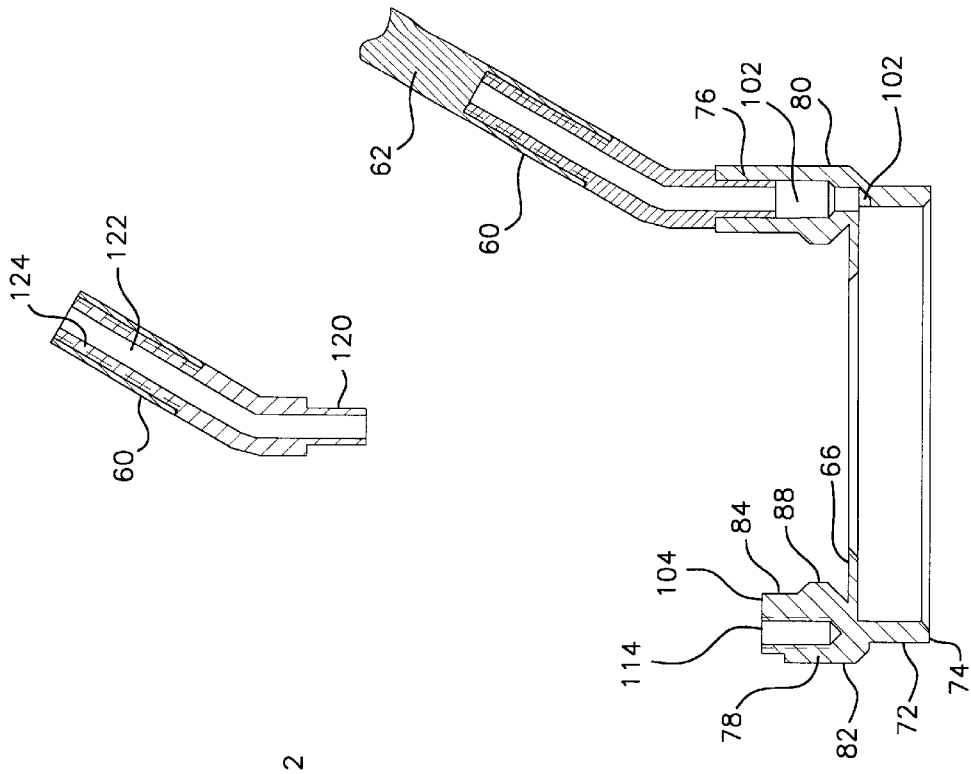
FIG. 6
FIG. 7
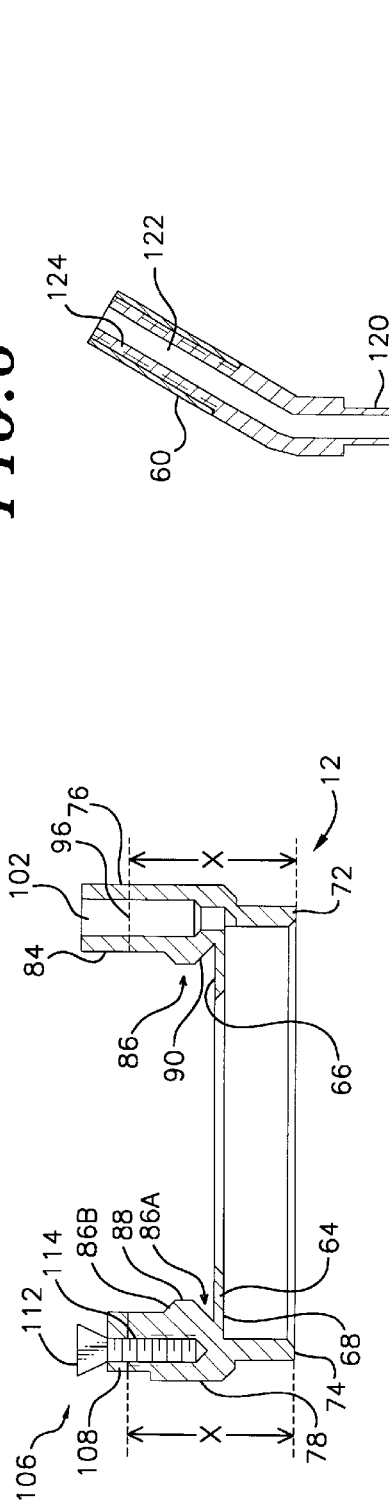
FIG. 5
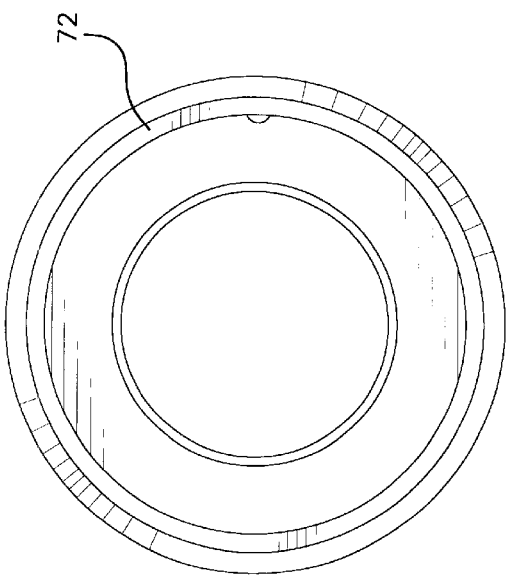
FIG. 8

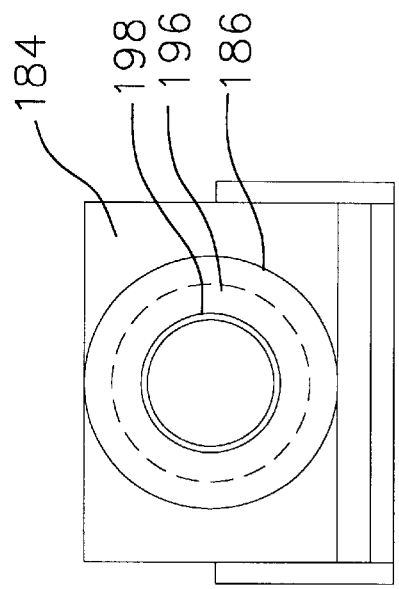
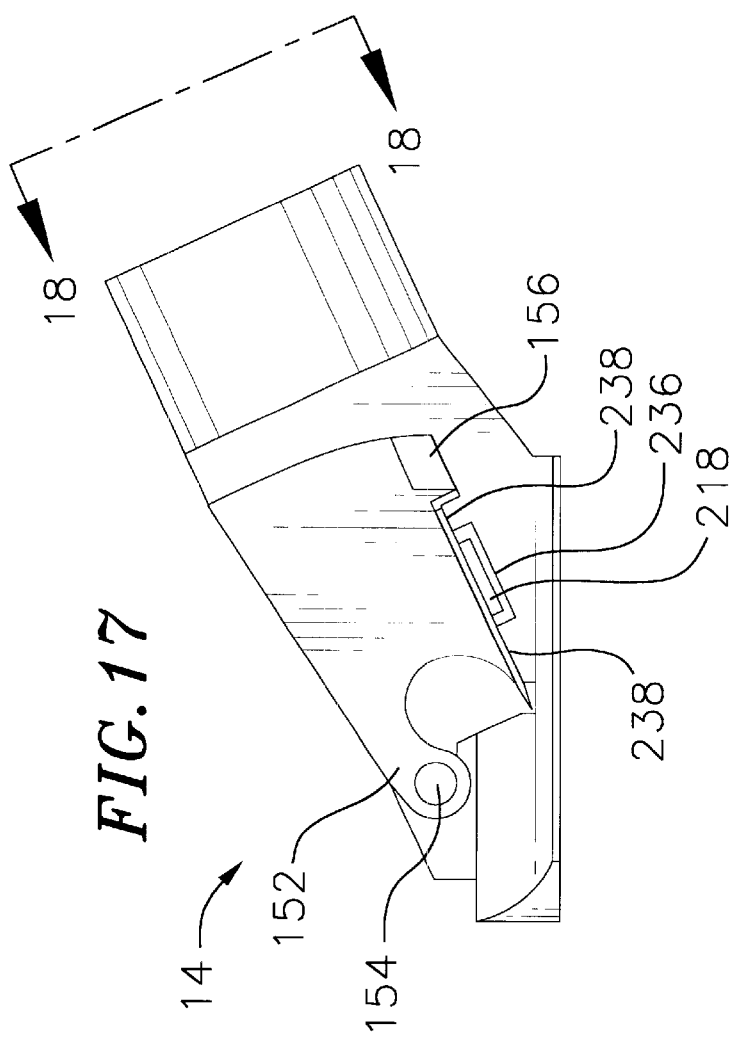

MICROKERATOME

BACKGROUND OF THE INVENTION

1. Field of the Art

The invention is directed to a corneal surgery apparatus. In particular, this invention is a microkeratome instrument for use in refractive surgery.

2. Discussion of Background and Prior Art

Correctable conditions of the optical system in the eye are known. Myopia (nearsightedness) is a condition where the visual images come to focus in front of the retina of the eye resulting in defective vision of distant objects. Hyperopia (farsightedness) is a condition in which visual images come to focus behind the retina of the eye and vision is better for distant objects than for near objects. Astigmatism is a condition in which light rays from a point fails to meet in a single focal point, resulting in a blurred and imperfect image. In the human eye this defect of vision due to astigmatism is typically due to a corneal irregularity.

Refractive surgery is a known method of treating myopia, hyperopia, astigmatism, and certain corneal abnormalities. This process involves reshaping various layers of the cornea to change the refractive surface thereof. Numerous methods of refractive surgery have been developed, including radial keratotomy (where radial slits are cut into the cornea to correct myopia), automated lamellar keratoplasty ("ALK", where a first flap is created in the upper layer of the cornea with a microkeratome, then additional corneal tissue is removed to correct vision), laser photorefractive keratectomy ("PRK"), among other methods. Presently, LASIK (the acronym for "laser assisted in situ keratomileusis"), has gained popularity. In the LASIK procedure, an excimer laser is used to reshape the cornea after a thin layer of the cornea (a corneal flap) is raised in a procedure called a keratectomy. The excimer laser is used to ablate selective areas of the cornea under the incision, and thereafter the corneal flap is returned to its position, where it quickly heals.

A critical part of the LASIK procedure is cutting a generally circular flap on the top surface of the cornea, in a procedure called a keratectomy. The device used to do this is the microkeratome. Numerous different styles of microkeratomes are available. These prior art microkeratomes include an eye engaging portion that has an aspiration ring for securing the eye engaging portion to the eye, an applanate plane against which the cornea of the eye will press flat against, and a rapidly oscillating blade placed in close proximity to the applanate plane which are used slice the thin corneal flap. These different styles of microkeratomes are designed to be used with a speculum. After the flap is cut and folded back, an excimer laser is used to remove corneal tissue under the cut flap and reshape the cornea. Thereafter, the flap is laid back on top of the excised area. Use of a speculum during keratectomy can cause patient discomfort, and cause involuntary eye movement.

Furthermore, in some presently available microkeratomes, a head portion with the microkeratome blade must be carefully aligned with the eye engaging portion after the eye engaging portion is fitted to the eye which can be difficult to do.

In other microkeratome designs, the head portion is engaged with the eye engaging portion prior to placement on the eye. However, these designs tend to be bulky, reduce access to the surgical field, and can be awkward to place and remove from the eye.

The prior microkeratomes also either do not permit simple adjustment of the size of the uncut corneal flap or have bulky mechanisms.

A further inadequacy with some prior microkeratome designs is that their motorized handpieces are noisy, which further raises the anxiety level of the patient and can cause eye movement.

Other shortcomings with some presently available microkeratome include the quality of the corneal flap created during the keratectomy, the need to calibrate the depth of the cut (e.g. by adjusting the position of the applanata plane), and the difficulty in easily and consistently selecting the desired corneal flap thickness from procedure to procedure.

Yet a further shortcoming of present microkeratomes is that they can be troublesome to clean and sterilize. Indeed, disposable microkeratomes are now available to reduce sterilization downtime.

There accordingly remains a need for an improved microkeratome that addresses the above concerns.

SUMMARY OF THE INVENTION

Most microkeratomes have some common elements. A positioning assembly with a suction ring is provided for application to the cornea of the eye and is temporarily fixed there by suction being applied. A considerable amount of suction is required to hold the suction ring in place, and as a result, the surgeon must carry out the keratectomy relatively quickly. The top surface of the base portion has a flat surface. A head portion is engaged with the base portion. The head portion has a rapidly moving blade provided therein and an applanate plate that is used to slice a very thin top layer of cornea. A motorized microkeratome handpiece attaches to the head portion and moves the blade.

The positioning assembly has two spaced apart guide walls and that are raised above a platform surface higher than guide walls of prior art designs. These two guide walls permit the surgeon to conduct the keratectomy without using a speculum to forceably hold the lids of the eye open since the raised walls themselves will prevent the lids from impinging on the surgical field during the keratectomy. With prior art microkeratomes, they sometimes impinge on the speculum, or worse yet, pinch the eye lid against the speculum, which can be very painful.

The guide walls of the positioning assembly include slide surfaces that interact with complementary slide surfaces of the head portion, including beveled entry points on the slide surfaces of the base portion and head portion. These beveled surfaces aid the surgeon in sliding the head portion into the positioning assembly quickly and securely after the positioning assembly is placed on the cornea and aspiration is applied to retain the positioning assembly in place. In prior designs, this has sometimes presented a challenge to the surgeon, particularly less experienced surgeons.

Another aspect of the invention includes the feature that the head portion has a base portion with an insert portion, with the insert portion being detachably and pivotally engaged with the base portion to allow for easy and through sterilization between uses of the microkeratome. By designing the insert portion to be detachably retained to the base portion, different insert portions can be provided for use with a standardized base portion. These different insert portions can accommodate specialized needs, including slightly different cutting depths.

Another feature of the invention is its compact and optionally adjustable stopping means used to prevent the head portion and its blade from pushing through the top layer of cornea and entirely cutting off the corneal flap.

Yet another feature of the invention that works in concert with the new design of microkeratome is a new design for a microkeratome handpiece that has a brushless DC motor, which generates more torque, a wider range of speeds (e.g. 5,000 rpm to 40,000 rpm), and does so more quietly, which further prevent the patient from becoming nervous during the refractive surgical procedure. As noted above, the more relaxed the patient is, the less chance there is of the patient's eyeball excessively moving during the procedure.

These and other aspects of the microkeratomes of the invention are further described below.

DESCRIPTION OF THE DRAWINGS

FIG. 5 is a cross-sectional view of the positioning assembly through view lines 5—5 of FIG. 4.

FIG. 6 is a cross-sectional view of the vacuum inlet tube.

FIG. 7 is another cross-sectional view of the positioning assembly with the vacuum inlet attached but with the optional adjustable stop removed.

FIG. 8 is a bottom view of the suction ring of the positioning assembly.

FIG. 17 is a side view of the head portion of the microkeratome of FIG. 11.

FIG. 18 is a rear view of the head portion of the microkeratome of FIG. 11.

DETAILED DESCRIPTION OF THE INVENTION

Figure 1:
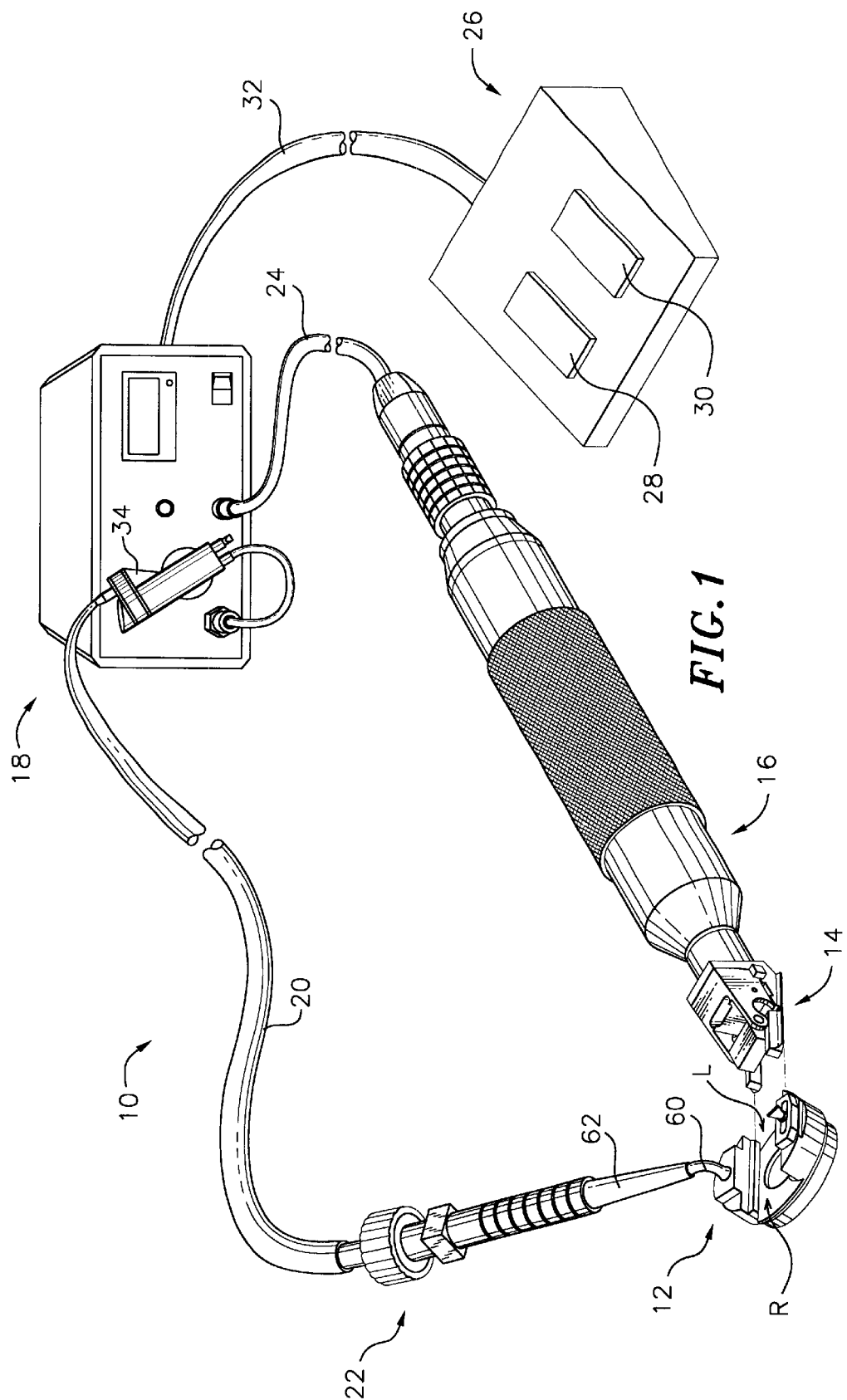
FIG. 1 perspective view of the microkeratome of the invention connected to a microkeratome handpiece and a voltage and vacuum supply unit with the microkeratome head portion detached from the positioning assembly.

Referring to FIG. 1, there is shown a microkeratome unit 10. Microkeratome unit 10 includes a positioning assembly 12, a head portion 14 attached to microkeratome handpiece 16, and a power and aspiration control unit 18. A vacuum line 20 connected to power and aspiration control unit 18 connects to a vacuum handle 22 on positioning assembly 12. A power cord 24 connects to microkeratome handpiece 16 and power and aspiration control unit 18. A foot pedal unit 26 has an aspiration control switch 28 and a microkeratome handpiece motor control switch 30 to permit a surgeon to control and turn on and off the amount of aspiration and voltage delivered to the motor in the microkeratome handpiece 16 (and thereby control the oscillating rpm of the microkeratome blade, as will be described further below.) Foot pedal control 26 is connected to power and aspiration control unit 18 with control line 32. Vacuum line 20 preferably connects to power and aspiration control unit 18 via a vacuum filter device 34.

Figure 2:
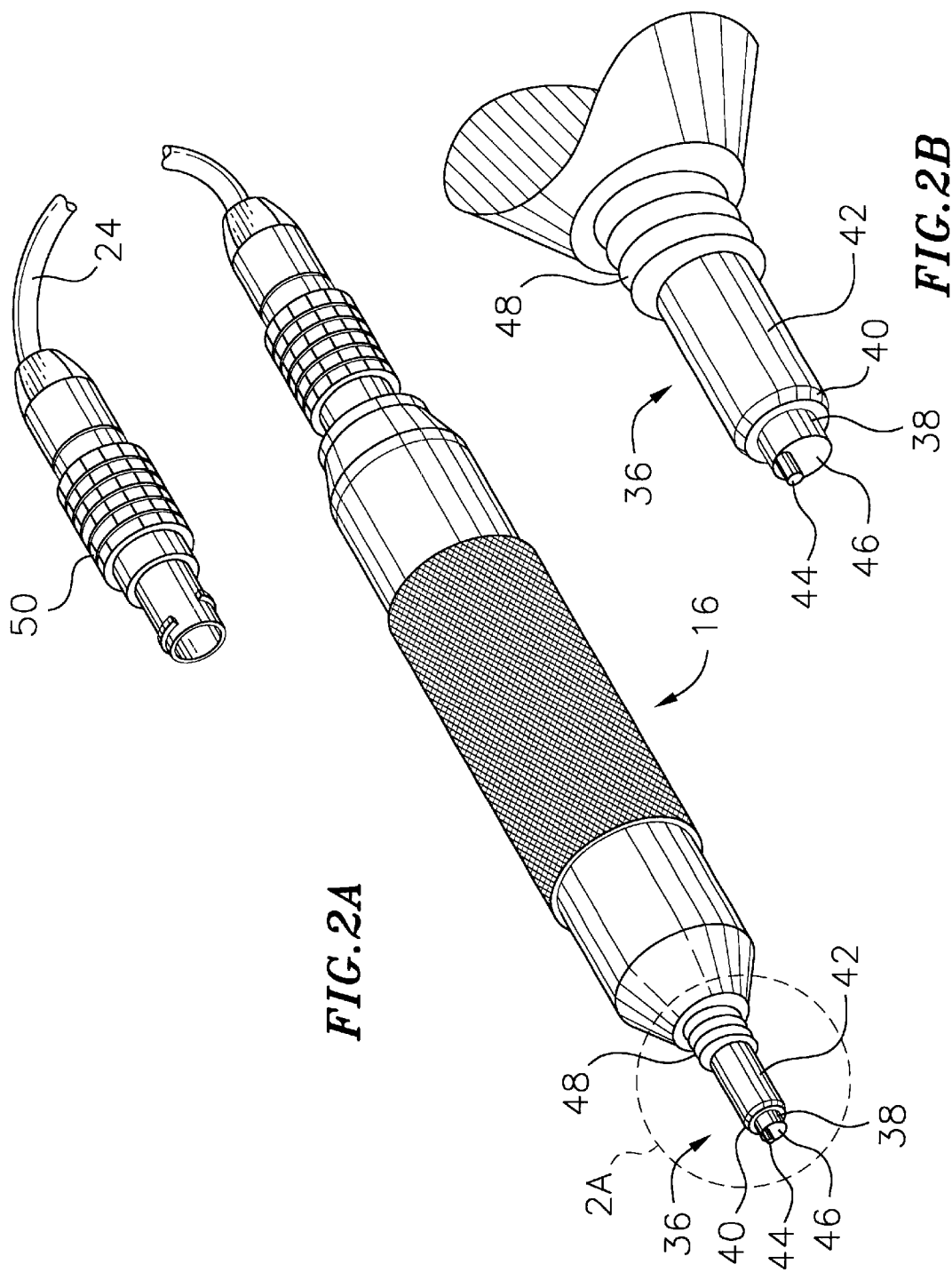
FIG. 2A is a perspective view of the microkeratome handpiece for use with the microkeratome of FIG. 1.
FIG. 2B is a detail of the distal region of the microkeratome handpiece of FIG. 2A in the dashed circle region.

FIG. 2A is a perspective view of microkeratome handpiece 16 and its detached power cord 24. FIG. 2B is a detail of distal region 36 of microkeratome handpiece 16 of FIG. 2A shown in the dashed circle region. A rotatable shaft 38 extends beyond a terminal end 40 of a distal extension 42. Terminal end 40 can preferably be beveled. Rotatable shaft 38 has a protrusion 44 extending therefrom a face 46 of rotatable shaft 38. Protrusion 44 is off center of the central axis of rotatable shaft 38, such that when rotatable shaft 38 rotates, protrusion 44 will oscillate from side to side and up and down. In lieu of the cylindrically shaped being protrusion 44, an elliptically shaped protrusion or some other shape could be utilized to provide for the oscillating tip. A detachable engagement means 48 is formed in distal region 36 of microkeratome handpiece 16, and can comprise a twist and lock means, such as helical threads formed rearwardly of distal extension 42. The function of detachable engagement means 48 will be explained further below. A quick attach power plug 50 is preferably provided at end of power cord 24, and is adapted to allow microkeratome handpiece 16 to be quickly connected and disconnected to power and aspiration control unit 18.

Figure 3:
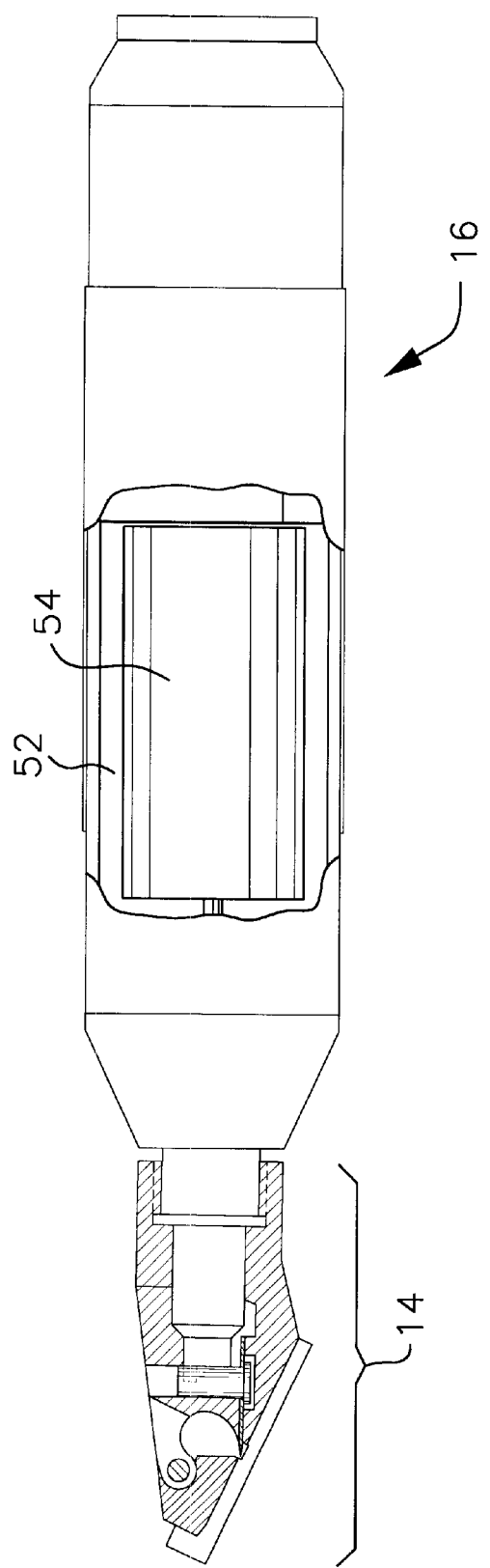
FIG. 3 is a partial cross-sectional view of the microkeratome's head portion connected to the microkeratome handpiece.

Turning to FIG. 3, there is shown a partial cross-sectional view of the microkeratome's head portion 14 connected to the microkeratome handpiece 16. Microkeratome handpiece 16 has an internal cavity 52 in which is located a motor 54. Motor 52 is preferably a variable speed brushless DC motor. Rotatable shaft 38 connects to and is adapted to be rotated by motor 52. At least protrusion 44 is adapted to be capable of pushed rearwardly in order to permit protrusion 44 to initially engage with and stay engaged with a microkeratome blade to oscillate the microkeratome blade during the keratectomy. This can be accomplished in different ways. For example, motor 54 can be spring loaded within cavity 52 (with rotatable shaft 38 being rotatable fixed to motor 54), protrusion 44 can be spring loaded relative to the distal end 36 of rotatable shaft 38, and/or at least a portion of rotatable shaft 38 can be spring loaded relative to motor 54 (which can mounted in cavity 52 so as to prevent excessive movement therein). As noted, use of a brushless DC motor is preferred because brushless DC motors can develop high torque at a wide RPM range. In a preferred embodiment of the invention, a brushless DC motor, such as Model No. 1628T, provided by Micro Me Electronics, of Clearwater, Fla. can be used. This motor (and similar motors) will operate at necessary torque levels between about 5,000 to 40,000 rpms, subject to the appropriate voltage being provided by power and aspiration control unit 18, as controlled by the surgeon operating microkeratome handpiece motor control switch 30. A more typical operating RPM range is about 15,000 RPMs. Another advantage of using a brushless DC motor 54 in microkeratome handpiece 52 besides the wide operating RPM range is that brushless DC motors are quieter than other types of motors (including AC motors, motors with brushes, and pneumatically driven motors.) The inventor has found that the quieter the motor, the less alarmed and the more relaxed the patient is when the motor is operated. A less alarmed patient translates into a patient who struggles and fights less with the surgeon. As a result, the surgeon will be better able to make more consistent and better quality corneal flaps during the keratectomy.

Figure 4:
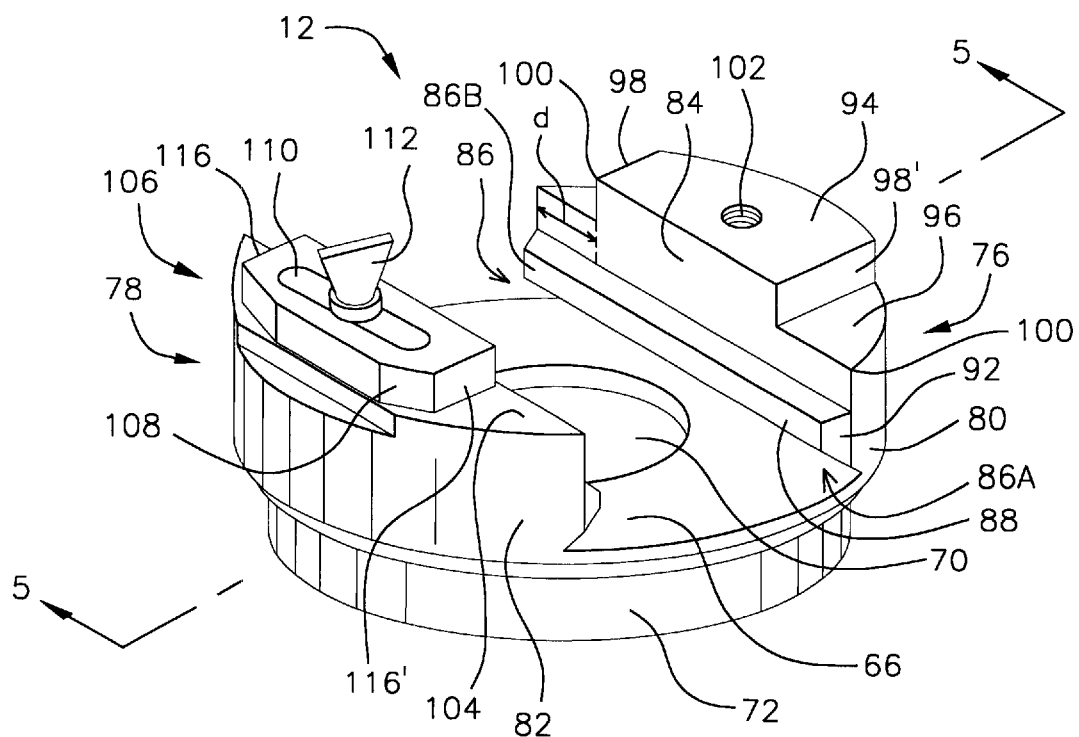
FIG. 4 is a perspective view of the microkeratome positioning assembly with the aspiration tube removed.
Figure 10:
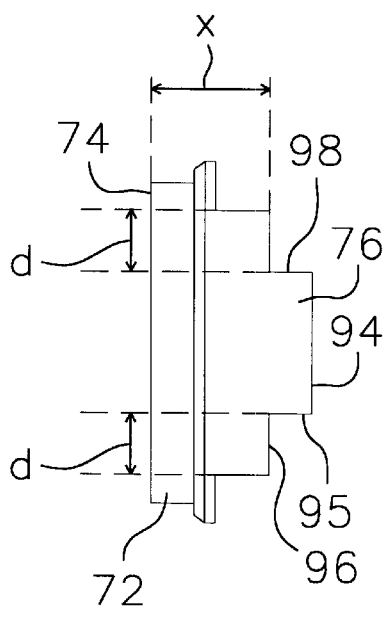
FIG. 10 is a front view of the first guide wall of the positioning assembly.
Figure 9:
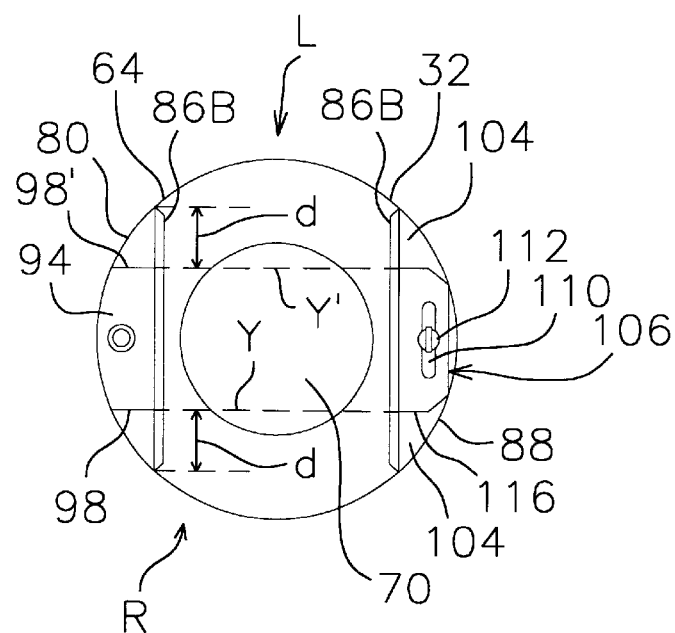
FIG. 9 is a top plan view of the positioning assembly with the vacuum inlet removed.

Referring to FIGS. 4–10, there are shown various view of microkeratome positioning assembly 12. FIG. 4 is a perspective view of positioning assembly 12 with its aspiration tube removed. FIG. 5 is a cross-sectional through view lines 5—5 of FIG. 4, FIG. 6 is a cross-sectional view of aspiration tube 60, FIG. 7 is a cross-sectional view of positioning assembly 12 with its aspiration tube 60 attached, with part of a vacuum handle 62 shown. Positioning assembly 12 has a platform 64 with an upper surface 66 and a lower surface 68. A corneal opening 70 is formed through platform 64. A suction ring 72 extends below lower surface 68, and has a lower edge 74 which is placed onto the surface of the patient's eyeball over the cornea during the keratectomy. A first and a second spaced apart guide wall 76 and 78, respectively, extend upwardly from upper surface 66 of platform and preferably have curved outer surfaces 80 and 82, respectively, and parallel straight inner surfaces 84. First sliding engagement means 86 are formed on parallel straight inner surfaces 84, and comprise slots 86A formed in parallel straight inner surfaces 84, and can also further preferably comprise wall skates 86B above slots 86A which extend inwardly from parallel straight inner surfaces 84. Wall skates 86B preferably have relatively narrow riding faces 88, and downwardly and inwardly slanting faces \90 which merge into slots 86A. Slots 86A and wall skates 86B extend across first and second guide walls 76 and 78, respectively, from end to end. Terminal ends 92 of wall skates 86B are preferably beveled. Other designs for first sliding engagement means 86 can be utilized, but as will be explained further below, wall skates 86B and particularly beveled wall skates 86B improve the ease with which head portion 14 is inserted into and moved relative to positioning assembly 12 after positioning assembly is placed on the patient's eyeball. As shown in FIGS. 4, 9 and 10, first guide wall 76 has an uppermost elevated platform 94 that rises off of secondary platform sections 96, which secondary platform sections 96 staddle uppermost elevated platform 94. Uppermost elevated platform 94 has stopping wall faces (or first guide wall protrusion) 98 and 98' set back a predetermined distance "d" from tip 100 of secondary platform sections 96. A vacuum aspiration port 102 in communication with suction ring 72 extends from uppermost elevated platform 94 down through first guide wall 76 and exits through platform 64 within suction ring 72. As shown in FIGS. 5 and 10, the top surface of secondary platform sections 96 is located at a distance "x" above lower edge 74 of suction ring 72. Second guide wall 78 has a top surface 104 that is likewise located at or approximately a distance "x" above lower edge 74 of suction ring 72. An optional adjustable stop means 106 can be provided to adjustably and lockably seat on top surface 104. In the embodiment shown in FIGS. 4, 5 and 9, adjustable stop means 106 comprises a slidable plate 108 with a slot 110 formed therethrough. A thumbscrew 112 screws into a threaded aperture 114 formed through top surface 104. Slidable plate 108 has two opposing end faces 116 and 116'. As best shown in FIG. 9, slidable plate 108 and its elongate slot 110 are sized such that slidable plate 108 can be moved and locked in place with thumbscrew 112 so that either of the two end faces 116 and 116' will be slightly forward of either imaginary dashed lines Y or Y', or left in the position shown in FIG. 9, wherein slidable plate 108 is positioned with its two end faces 116 and 116' between imaginary dashed lines Y or Y'.

Referring back to FIG. 6, a cross-sectional view of aspiration tube 60 is shown. It has a lower, insert end 120 which fits into inlet end of vacuum aspiration port 102, and is attached thereto (e.g. by permanent means, such as welding, adhesives, or by thread means.) A passageway 122 extends through aspiration tube 60, and upper end of aspiration tube 60 is preferably threaded 124 to engage with vacuum handle 62 which is threaded with mating threads, (as shown in FIG. 7.)

Turning to FIG. 8, a bottom view of positioning assembly 12 is shown, and shows suction ring 72, bottom surface 64 of platform, corneal opening 70, and opening of vacuum aspiration port 102.

Figure 11:
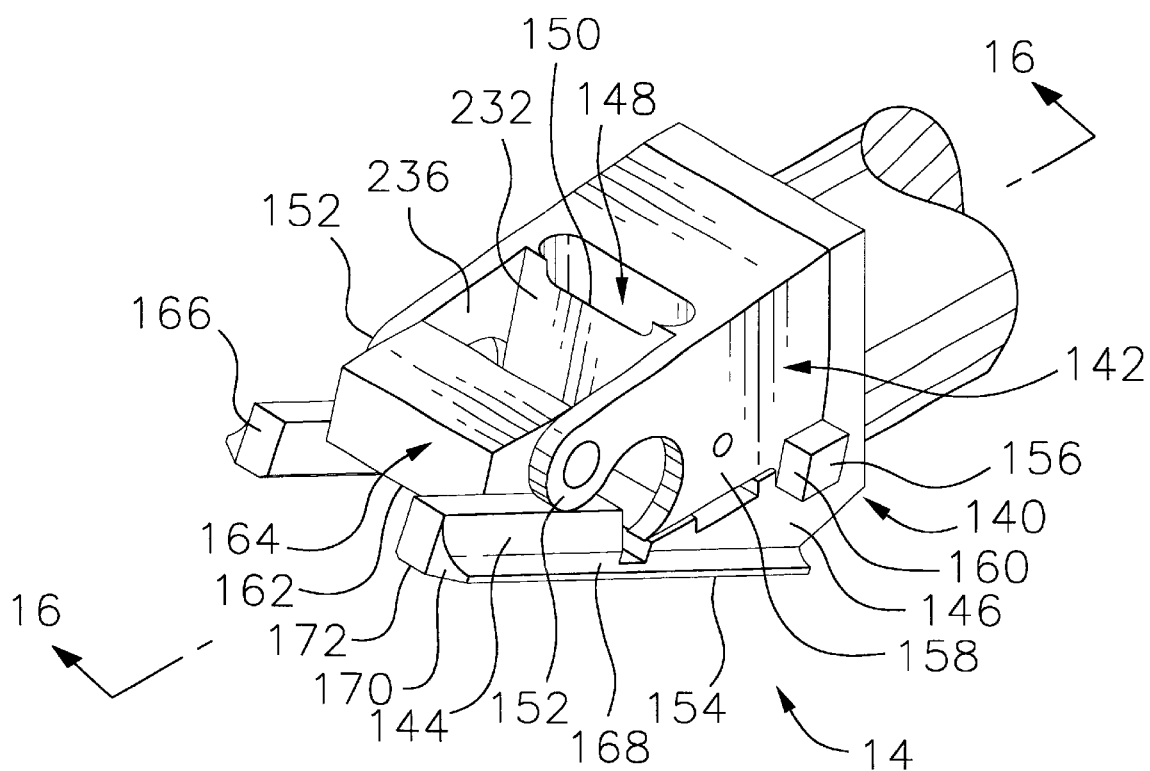
FIG. 11 is a perspective view of the head portion with part of the microkeratome handpiece shown attached.

Referring to FIG. 11 there is shown a perspective view of the head portion 14 with part of the microkeratome handpiece 16 shown. Head portion comprises a base portion 140 and an insert portion 142. Second sliding engagement means 144 are formed on and extend from sides 146 of base portion 140. A blade retention slot 148 is formed in insert portion 142, and has a partition wall 150 formed in front of blade retention slot 148. A pair of fingers 152 are formed at a front of insert portion 142, and a pivot pin 154 fits between the pair of fingers 150. Insert portion 142 is at least partially opened in front of partition wall 150. Head portion protrusions 156 extend from sides 158 of insert portion 142, and have a forwardly facing contact face 160. Second sliding engagement means 144 comprise base portion skates which project outwardly from sides 146 and downwardly from a bottom surface 162 of base portion 140. Each base portion skate 144 also preferably has an extension portion 166 which extends forward of a front 164 of base portion. Base portion skates 144 have prism-shaped extension portions 168, and the fronts 170 of prism-shaped extension portions 168 are preferably beveled. Base portion skates 144 have bottom surfaces 172.

Figure 12:
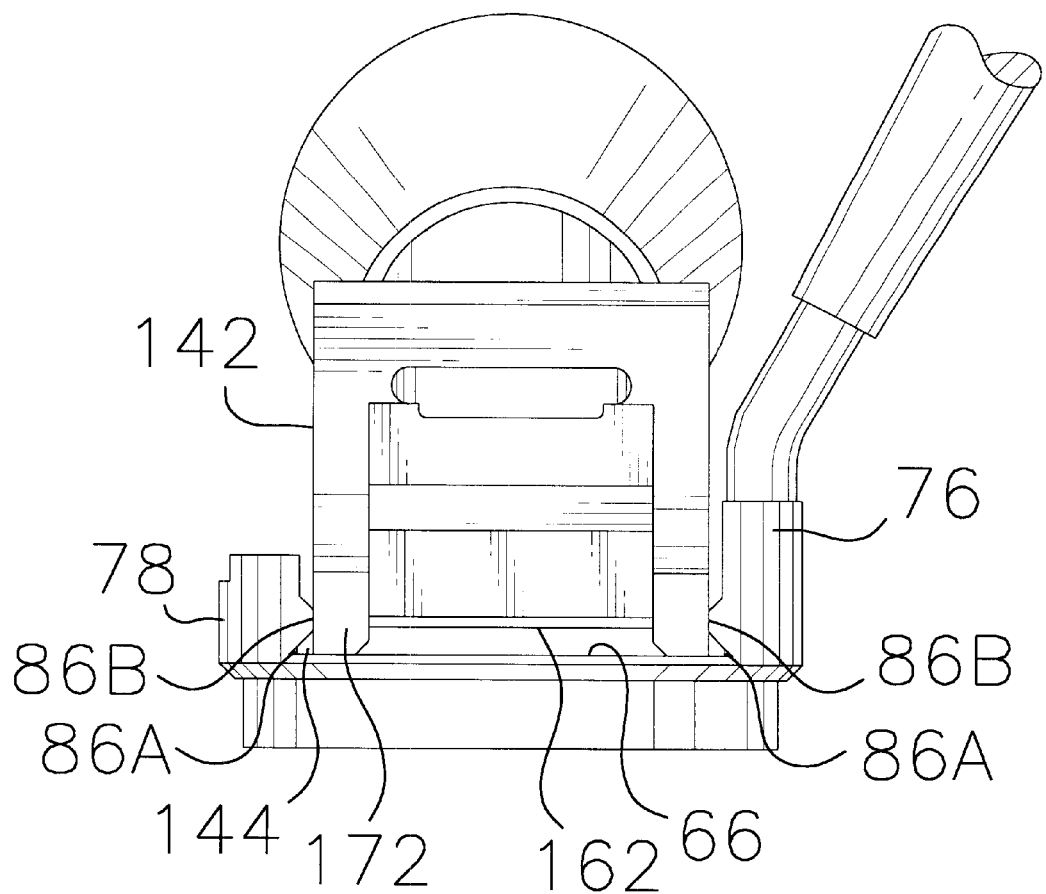
FIG. 12 is a front view of the head portion engaged with positioning assembly.

Turning to FIG. 12, a front view of head portion 14 inserted into positioning assembly 12 is shown, and the slidably interaction of base portion skates 144 of base portion 142 with slots 86A and wall skates 86B on first and second guide walls 76 and 78, respectively, and bottom surfaces 172 of base portion skate 144 on upper surface 66 of platform 64. As can be seen, bottom surface 162 of base portion 140 is thereby spaced above upper surface 66 and corneal opening 70 in platform 64. Slots 86A and wall skates 86B on first and second guide walls 76 and 78 are sized, shaped, and spaced apart from each other and are adapted to permit base portion skates 144 of base portion 142 to smoothly and slidable engage therewith.

Figure 13:
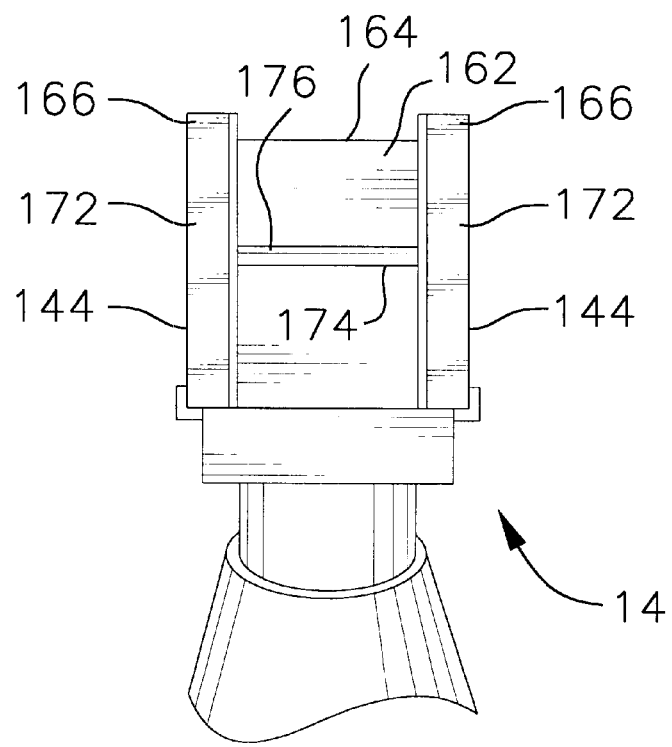
FIG. 13 is a bottom view of the head portion.

Turning to FIG. 13, a bottom view of head portion 14 is shown, and shows bottom surface 172 of base portion skates 144, extension portion 166 extending beyond front 164 of base portion, bottom surface 162 of base portion, a base slot 174, and a cutting edge of a microkeratome blade 176 projecting through base slot 174.

Figure 14:
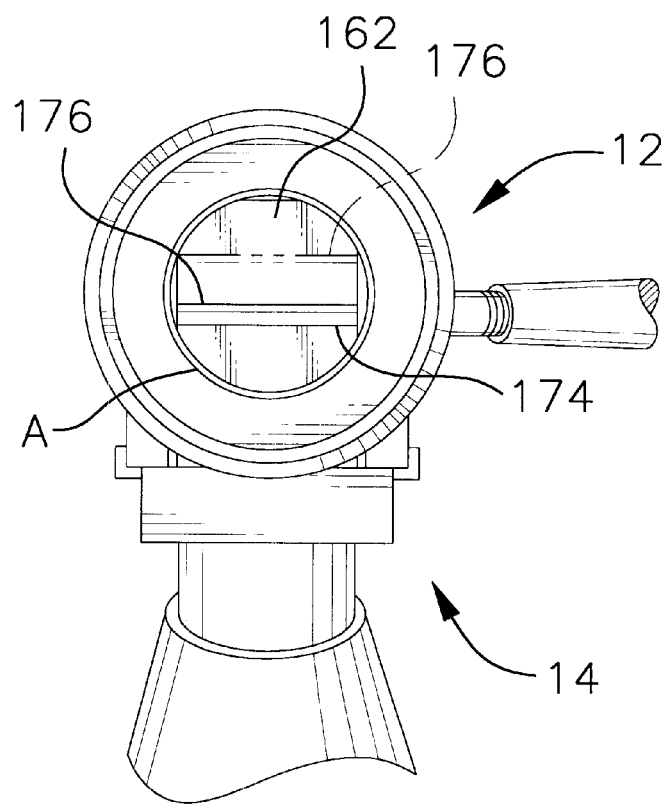
FIG. 14 is a bottom view showing the head portion engaged with positioning assembly.

FIG. 14 is a bottom view of head portion 14 engaged with positioning assembly 12, and shows a portion of bottom surface 162 of base portion, base slot 174, and cutting edge of the microkeratome blade 176 projecting through base slot 174.

Figure 15:
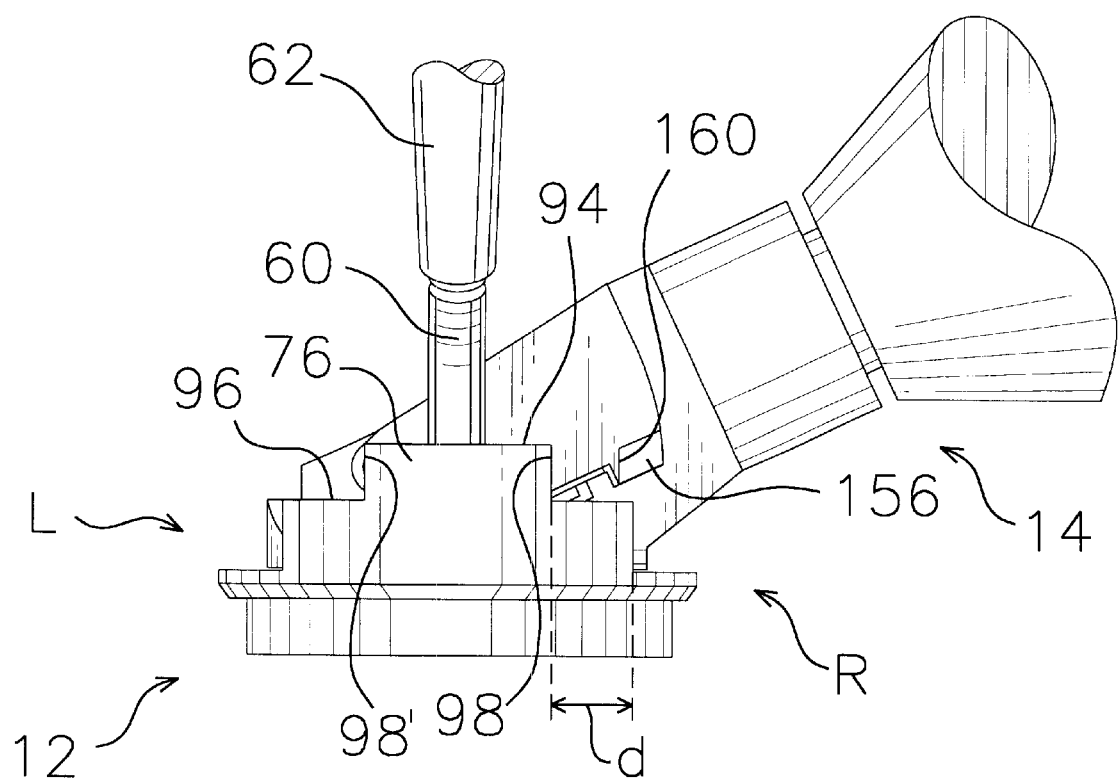
FIG. 15 is a side view of the head portion engaged with positioning assembly.

FIG. 15 is a side view of head portion 14 slidably engaged with positioning assembly 12, and illustrate how head portion protrusions 156 and its contact face 160 is elevated above secondary platform section 96 and how it impinges a trailing stopping wall face 98 of uppermost elevated platform 94, and thereby prevents head portion 14 from being advanced any further (see FIG. 14, showing the head portion 14 maximally advanced into assembly portion 12, with microkeratome blade spaced a considerable distance away from forwardmost point "A" of corneal opening 70.) This results in a uncut corneal flap remaining after the keratectomy. The combination of head portion protrusions 156 and stopping wall face 98 form a stopping means. As can clearly be seen in FIGS. 1, 9 and 15 microkeratome head portion 14 can be inserted from either a left entry side "L" or a right entry side "R" of positioning assembly 12. In FIG. 1, head portion is being prepared for engagement with positioning assembly 12 through left entry side "L". In FIG. 15, head portion is fully engaged with positioning assembly 12 through right entry side "R".

Referring back to FIG. 9, if adjustable stop means 106 is slided and locked in place with its end face 116' forward of imaginary line Y', and the head portion is inserted through left entry side "L", then its head protrusion 156 will impinge on leading end face 116' rather than on the leading stopping wall face 98' of uppermost elevated platform 94 (not shown). Conversely, if adjustable stop means 106 is slide and locked in place with its end face 116 forward of imaginary line Y, and the head portion is inserted through right entry side "R", then its head protrusion 156 will impinge on end face 116 rather than on the stopping wall face 98 of uppermost elevated platform 94. The adjustable stop means 106 can thereby be used to limit the range of motion of head portion 14 relative to positioning assembly 12, and thereby can be used to form a larger uncut corneal flap during the procedure. A discussion of the keratectomy procedure will follow further below.

Figure 16:
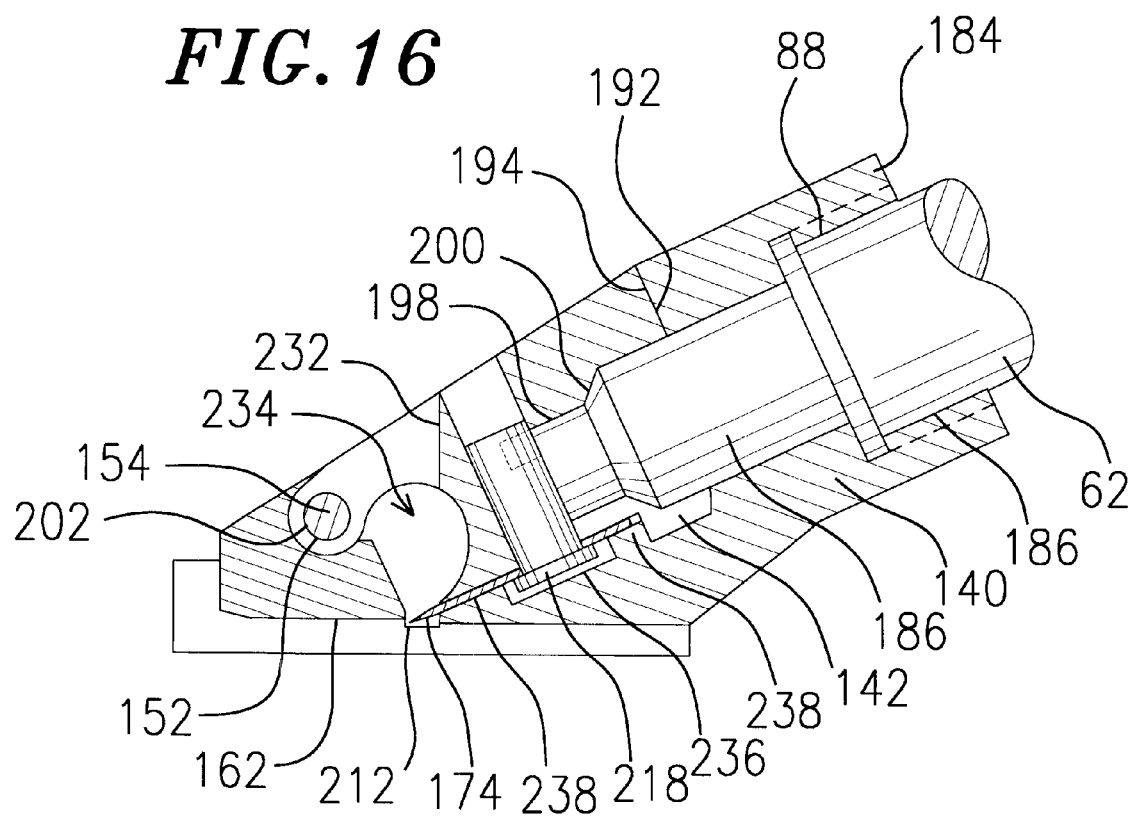
FIG. 16 is a cross-sectional view of the head portion through view lines 16—16 of FIG. 11 of the head portion and part of the microkeratome handpiece holding a microkeratome blade, in the microkeratome's operate mode.
Figure 21:
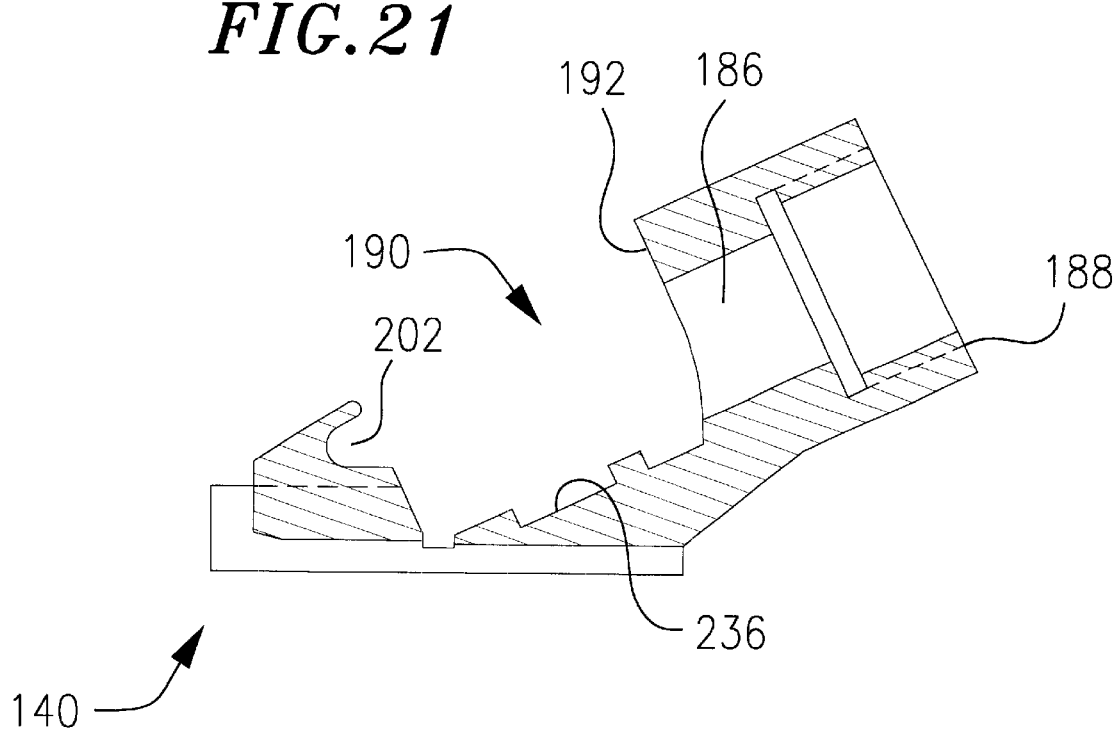
FIG. 21 is a cross-sectional view of the base portion of the microkeratome with the insert portion removed.
Figure 22:
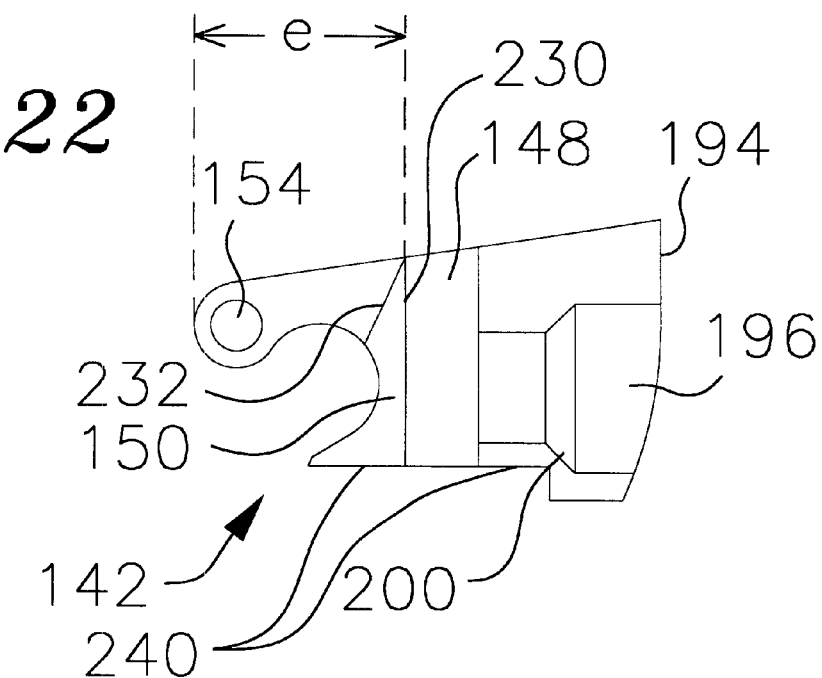
FIG. 22 is a cross sectional view of the insert portion of the microkeratome.

Turning to FIG. 16, a cross-sectional view of head portion 14 and part of microkeratome handpiece 62 through view lines 16—16 of FIG. 11 is shown. Rear 184 of base portion has an alignment aperture 186 formed therein, with first attachment means 188 formed therein. First attachment means 188 can comprise threads formed on alignment aperture 186, twist and lock means, or other means. In the preferred embodiment, first attachment means 188 comprises coarse threads formed in aperture 186. Alignment aperture 186 extends forwardly into a cavity 190 of base portion 140, as is best shown in FIG. 21, and is sized to slidably receive distal extension 42 of microkeratome handpiece 16. Detachable engagement means 48 rearward of distal extension 42 detachably engages with first attachment means 188, and allows microkeratome handpiece 16 to be detachably engaged with head portion 14. Where alignment aperture 186 extends into cavity 190, the surface 192 is arcuate. Rear face 194 of insert portion is arcuate, and smoothly and pivotally fits adjacent to surface 192. As best shown in FIGS. 16 and 22, an insert portion axial aperture 196 extends from rear face 194 of insert portion and extends into communication with blade retention slot 148. Insert portion axial aperture 196 preferably closely conforms in shape to distal extension 42 of microkeratome handpiece, namely, it has a reduced diameter area 198 through which rotatable shaft 38 can rotatably pass, and preferably a beveled transition region 200 between insert portion axial aperture 196 and reduced diameter area 198, which will closely fit with beveled terminal end 40 of distal extension 42. Fingers 152 carry a pivot pin 154, which pivot pin 154 pivotally engage with a finger engagement recess 202 formed at the front end of base portion. In FIG. 16, a microkeratome blade 176 is shown placed in blade retention slot 148.

Figure 20:
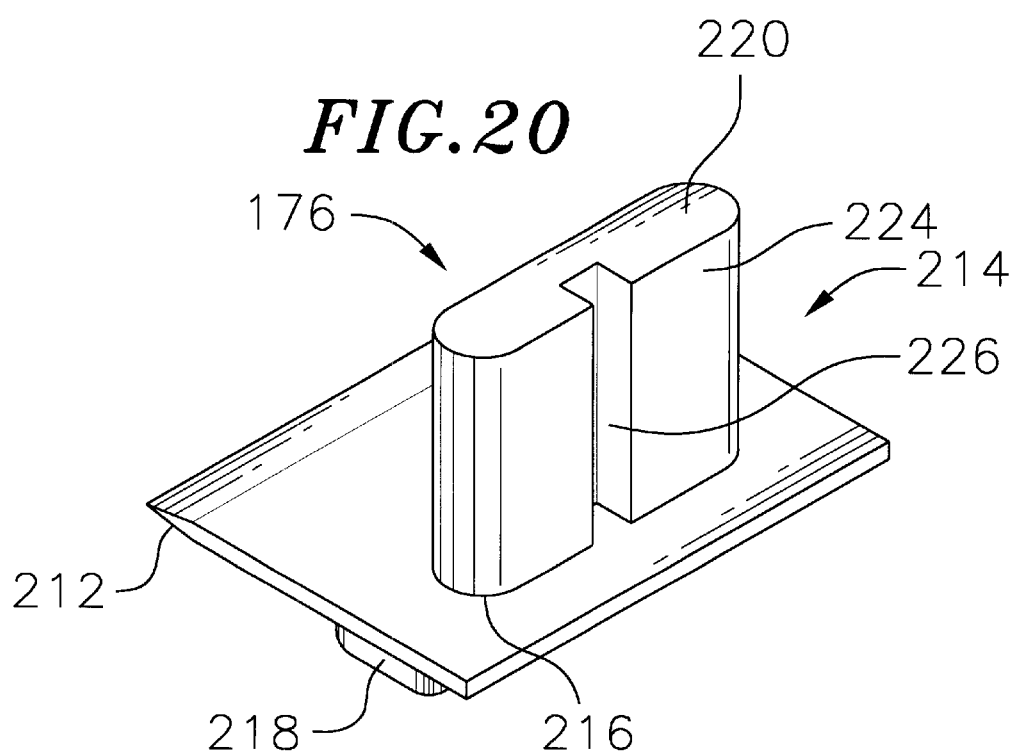
FIG. 20 is a perspective view of a microkeratome blade used with the microkeratome of the invention.

Turning to FIG. 20, a perspective view of the microkeratome blade 176 used with the microkeratome of the invention is shown in detail. Microkeratome blade 176 has a blade portion 210 with a cutting edge 212. An insert 214 is provided passes through an aperture 216 formed in blade portion 210. Insert 214 has a base 218 which seats on an underside of the blade portion 210, and a riser 220 which extends above an upper surface of blade portion 210. Riser 220 has a flat front face 222 and a rear face 224 with a microkeratome handpiece tip engagement means 226, such as a vertical slot. Cutting edge of blade 212 extends a predetermined and known distance forward of flat front face 22 of riser.

Turning back to FIG. 16, protrusion 44 will movably ride in vertical slot 226 in riser 220 of insert 214 of microkeratome blade 176. If when microkeratome handpiece 16 is first engaged with head portion 14 and protrusion 44 is not in horizontal alignment with vertical slot 226 of microkeratome blade 176, it will press against rear face 224 of riser 220. Because of the forward and backward movability of protrusion 44 relative to vertical slot 226, when motor 54 turns rotatable shaft 38, protrusion 44 will oscillate from side-to-side, and almost instantly snap into vertical slot 226, where it will remain for the entire procedure. Blade retention slot 148 in insert portion 142 is located behind the partition wall 150. Partition wall 150 has a flat, rearward face 230 located a predetermined distance "e" away from the front of the insert portion (as best shown in FIG. 22) and is positioned at an acuate angle relative to the lower planar face 162 of the base portion when insert portion 142 is engaged with the base portion 140 in the operate mode. Partition wall 150 has a slanted front face 232 and insert has an opened region 234 in front of partition wall. This opened region 234 is where the corneal flap will extend up into during the keratectomy. Base portion 140 has base insert cutaway 236 to accommodate base 218 of microkeratome blade 176. Blade riding surfaces 238 are formed on base portion on both sides of base insert cutaway 236 and support bottom surface of the microkeratome blade 176, and blade riding surfaces 240 on underside insert portion 142 on both sides of blade retention slot 148 which permit microkeratome blade 176 to slide from side to side, but not to vibrate up and down. Flat front face 222 of blade insert slidably rides on flat, rearward face 230 of partition wall 150. Microkeratome blades tip 212 will thus extend through base slot and project slightly below bottom surface 162 of base portion. As noted above, since cutting edge 212 of microkeratome blade 176 extends a predetermined and known distance forwardly of flat front face 22 of riser, and since partition wall 150 has a flat, rearward face 230 located a predetermined distance "e" away from the front of the insert portion, the exact distance which cutting edge 212 of microkeratome blade 176 extends below bottom surface 162 of base portion can be precisely set without recalibration between uses of the microkeratome. Indeed, with this design, a plurality of different insert portions 142 can be provided with slightly different predetermined distances "e", but with the same other dimensions if the surgeon should desire to change the thickness of the corneal flaps to be formed during the keratectomy. The implications of this design is that manufacturing costs of the microkeratome can be reduced, and the precision and reproducibility of the thickness of the corneal flaps can be maintained over the life of the microkeratome, without constant need for calibration or adjustment. This saves the surgeon and medical staff considerable time and presents less opportunities for mistakes to possibly occur.

FIG. 17 is a side view of the head portion 14 in its operate mode of the microkeratome of FIG. 11, and shows a base insert cutaway 236, base 218 and blade portion 210 of microkeratome blade 176 riding on blade riding surfaces 238 and 240.

FIG. 18 is a rear view of the head portion of the microkeratome of FIG. 11 and shows alignment aperture 186, insert portion axial aperture 196 and reduced diameter aperture 198.

Figure 19:
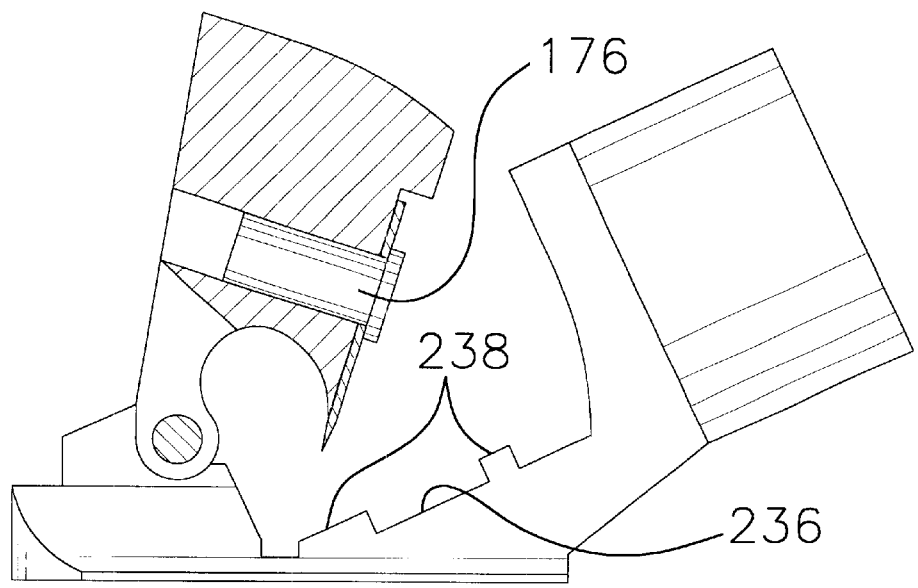
FIG. 19 is a side view of the head portion of the microkeratome holding a microkeratome blade in its opened mode for access to the microkeratome blade and for detaching the insert portion from base portion.

FIG. 19 is a side view of the head portion 14 holding a microkeratome blade 176 in its opened mode for inserting microkeratome blade and for detaching insert portion 142 from base portion 140. As shown, when insert portion 142 is swung up high enough off of base portion 140, its pivot pin 154 can be detached from finger engagement recess 202. Beside the above referenced ability to use a single base portion 240 with a plurality of different insert portions 142, another advantage in making the insert portions 142 so readily detachably from base portion is that it permits the head portion to be better cleaned and sterilized between uses of the microkeratome.

FIG. 21 is a cross-sectional view of base portion 140, and better shows finger engagement recess 202 into which pivot pin 154 is adapted to pivotally engage.

Figure 23:
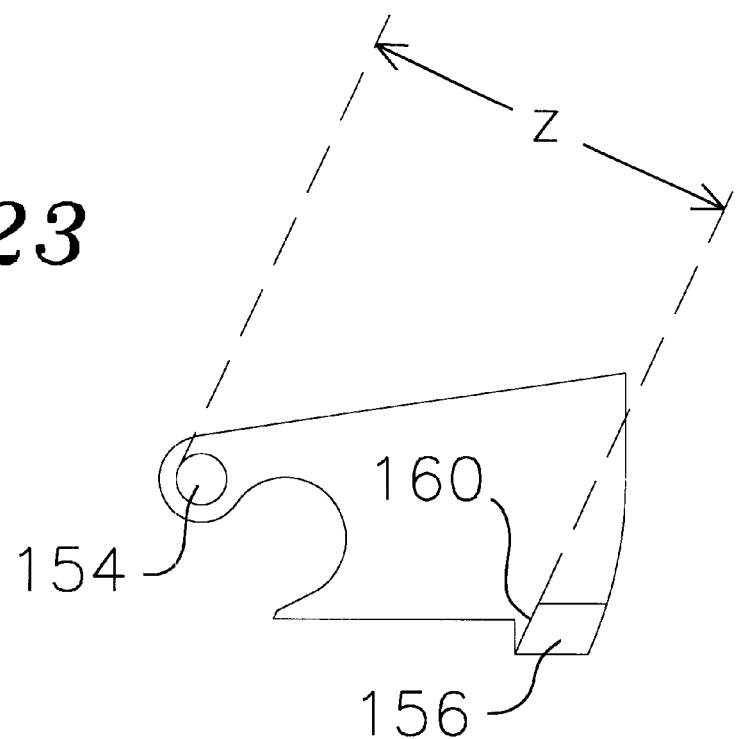
FIG. 23 is a side view of the insert portion of the microkeratome.

FIG. 22 is a cross-sectional side view of insert portion 142, and FIG. 23 is the same view, but not in cross-section. Contact face 160 of head portion protrusions 156 are shown a predetermined distance "z" away from the pivot pin. By changing the size and position of the head portion protrusion, the distance head portion 14 can be slide into positioning assembly 12 can be varied. Providing a plurality of insert portions 142 having different distances "z" can be used to control the size of the uncut corneal flap.

Figure 24:
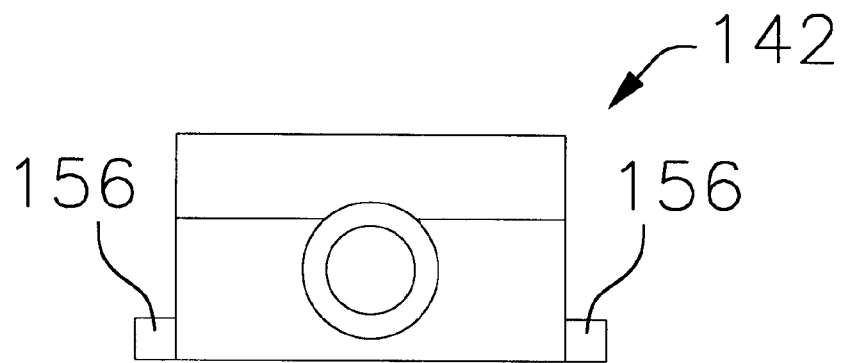
FIG. 24 is an end view of the insert portion of the microkeratome.

FIG. 24 is a back view of insert portion 142 and shows both head portion protrusions 156.

Figure 25:
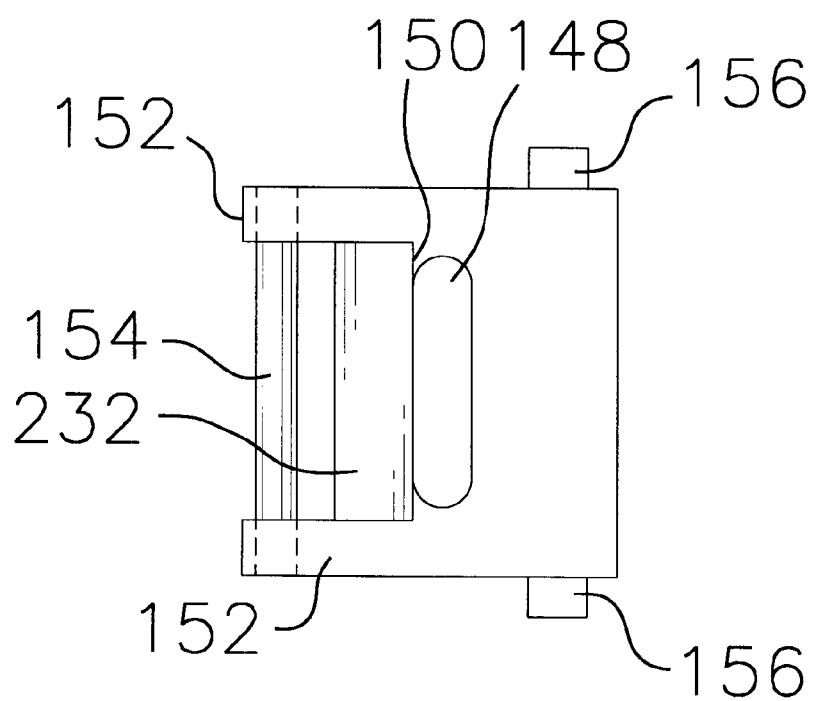
FIG. 25 is an top view of the insert portion of the microkeratome.

FIG. 25 is a top view of insert portion 142 and best shows pivot pin 152 retained by finger 152, blade retention slot 148, partition wall 150 and its slanted front face 232, and head portion protrusions 156.

Having described the main features of the invention, the operation of the microkeratome during a keratectomy is now more fully explained. During the keratectomy, the surgeon will first place the positioning assembly 12 on the cornea of the patient's eye. The surgeon will then activate the power and aspiration unit control unit 18 and apply suction through the vacuum line 20, to the aspiration tube 60. This causes the positioning assembly 12 to force itself down onto the cornea of the eyeball, and temporarily draws up the cornea of the eyeball through the corneal opening 70 in the positioning assembly 12 and above the upper surface of 66 of the platform. While the positioning assembly 12 is seated on the surface of the patient's eyeball, the surgeon then will grasp the microkeratome handpiece 62 connected to the head portion 14, and slidably engage the extension portions 166 of the head portion 14 with the positioning assembly 12 through its left entry side "L" or right entry side "R" that is furthest from the patient's nose. The design of the slots and skates with their beveled ends aids the surgeon in quickly and easily engaging the head portion 14 with the positioning assembly 12. Once engaged, the surgeon will activate the motor 54 in the microkeratome handpiece 16 by activating microkeratome handpiece motor control switch 30. This will cause the rotatable shaft 38 to rotate, which causes the protrusion 44 to oscillate horizontally, and oscillate the microkeratome blade 176 at a high speed. As the surgeon slides the head portion 14 forwardly, the bottom surface 162 of base portion will impinge on the surface of the eyeball, the cutting edge 212 of the microkeratome blade will slice a thin and predetermined top layer of the cornea. This sliced region of cornea will enter the base slot 174 forward of cutting edge, and will pass up into opened region 234. After the corneal flap is formed, the surgeon will turn off the motor, and thereby stop the blade from cutting. The surgeon will then withdraw the base portion from the positioning assembly. Doing so causes the corneal flap just formed to be withdrawn from the opened region 234. The surgeon will then flip the corneal flap aside to expose the cut surface of the cornea, and further carry out the refractive procedure, be it LASIK or another procedure.

As noted above, the distance "x" between tops of the first and second guide walls and the lower edge 74 of suction ring 72 is high enough so that the positioning assembly 12 can be applied to the patient's eyeball without any need to use a speculum to hold the patient's eyelids open during the keratectomy (since the eyelids will be restrained by the preferably curved and smooth guide walls and will be prevented from moving over the top of positioning assembly.) The smooth outer contour of the microkeratome of the invention further allows better entry and exit into the patient's eye.

Use of a speculum to force the patient's eyelids open can cause nervousness in some patients, and cause reflexive and involuntary movement of the eyeball. Indeed, if a speculum is used pinching of the patient's eyelids can sometimes occur. If there is excessive movement of the eyeball during the keratectomy, there is an enhanced risk of suction loss. Suction loss during the keratectomy can result in variety of problems in corneal flap formation, including incomplete flap (wherein the corneal flap does not extend far enough), irregular flap (wherein the desired generally symmetrical circular flap is not achieved), or severely irregular thickness in the corneal flap formed. Each of these problems require that the procedure be immediately halted, and that the patient's eye be allowed to heal before another attempt is made at a later date. Indeed, even if the thickness in the corneal flap formed is not so irregular as to force termination of the procedure, irregularities in the thickness in the cut, and excessively rough cutting can cause the patient to experience excessive haze, halo effects, and other visual side effects during the healing process. Accordingly, anything that reduces patient anxiety and reduced movement of the patient's eyeball contributes to improved results.

As also noted above, the motor 54 in the microkeratome handpiece of the invention is a quiet brushless DC motor. The lower noise of microkeratome handpiece further reduced patient anxiety.

The microkeratome of the invention utilizes a much smaller and optional adjustable stops as compared to bulky stops of prior microkeratomes. This improves access to the surgical field, and further allows the surgeon to follow movements of the patient's eyeball during the keratectomy, rather than fight or struggle with the patient to control the position of the eyeball.

Numerous variations and modifications within the spirit of the present invention will of course occur to those of ordinary skill in the art in view of the preferred embodiments that have been disclosed herein. Such variations, as well as any other systems embodying any of the following claims, all remain within the scope of the present invention.

What is claimed is:

1. A microkeratome adapted to be used with a microkeratome handpiece with an oscillating tip and a microkeratome blade, the microkeratome being for use in carrying out a keratectomy of a patient's eyeball to create a corneal flap, the microkeratome comprising:
   a) a positioning assembly having a platform with an upper surface and a lower surface with a corneal opening formed therethrough, the lower surface comprising a suction ring for application to the surface of the patient's eyeball around the cornea, a vacuum aspiration port in communication with the suction ring, and first and a second spaced apart guide walls extending upwardly from the upper surface of the platform and having outer surfaces, and parallel inner surfaces, the first and the second spaced apart guide walls being high enough to prevent a patient's eyelids from passing over the upper surface of the positioning assembly, the guide walls having first sliding engagement means formed on the inner surfaces thereof;
   b) a microkeratome head portion comprising, a base portion and an insert portion,
      the base portion comprising a lower planar face with a base slot extending therethrough, a front portion, a rear portion, opposing sides having second sliding engagement means formed thereon adapted for slidably engaging the head portion with the first sliding engagement means on the first and second guide walls such that the lower planar face will slide above the upper surface of the platform of the positioning assembly, and a cavity which communicates with the base slot, the rear portion having an alignment aperture formed therethrough, and
      the insert portion comprising a blade retention slot for slidably receiving a microkeratome blade, the insert portion fitting within the cavity of the base portion and having a front and a rear, an aperture formed through the rear which aligns with the alignment aperture formed in the base portion when the insert portion is engaged with the base portion in an operation mode; and
   c) a stop means for preventing the head portion from passing completely through the positioning assembly to thereby leave an uncut section of corneal flap after completing the keratectomy.

2. The microkeratome of claim 1, wherein the distance from a top of the second guide wall and a bottom surface of the suction ring is at least 3.5 mm.

3. The microkeratome of claim 1, wherein the distance from a top of the second guide wall and a bottom surface of the suction ring is preferably between 4 mm and 12 mm.

4. The microkeratome of claim 1, wherein the stop means comprises a first guide wall protrusion on the first guide wall and a head portion protrusion extending from one of the base portion and the insert portion.

5. The microkeratome of claim 4 wherein the head portion protrusions extend from both sides of the insert portion near its rear.

6. The microkeratome of claim 5, wherein the size, shape and position of the head portion protrusions can be varied to determine how far the head portion can be advanced into the positioning assembly.

7. The microkeratome of claim 1, further comprising an adjustable stop means, the adjustable stop means comprising a slider portion adapted to be moved and locked in longitudinal positioning on a top surface of the second guide wall, and adapted to engage with a protrusion extending from one of the head portion and insert portion.

8. The microkeratome of claim 1, wherein the first sliding engagement means comprises horizontal slots formed on the inner surfaces of the first and second guide walls that extend between ends of the first and second guide walls, and the second sliding engagement means comprise skates which are slidably engageable with the horizontal slots, the slides extending outwardly from the sides and downwardly below the lower planar face of the of the base portion.

9. The microkeratome of claim 1, wherein the ends of the first and second guide walls are beveled and front ends of the skates are beveled, the bevels permitting easy engagement of the microkeratome head portion with the positioning assembly when the positioning assembly is placed on the patient's eyeball.

10. The microkeratome of claim 1, wherein the first and a second spaced apart guide walls of the positioning assembly have curved outer surfaces.

11. The microkeratome of claim 1, wherein the insert portion is adapted to be pivotally and detachably engaged in the cavity of the base portion in the operation mode, and is also adapted to be completely separated from the base portion without the use of any tools and may be cleaned and sterilized between use of the microkeratome.

12. The microkeratome of claim 11, wherein the insert portion has a pivot rod at the front which pivotally engages with finger engagement recess on the base portion.

13. The microkeratome of claim 1, wherein the microkeratome blade comprises a blade portion with a cutting edge and an insert which engages with an aperture formed in the blade portion, the insert having a base which seats on an underside of the blade portion and a riser, the riser having a flat front face and a rear face with a handpiece tip engagement means, and wherein the blade retention slot in the insert is located behind a partition wall, the partition wall having a flat, rearward face located a predetermined distance away from the front of the insert and being positioned at an acuate angle relative to the lower planar face of the base portion when the insert is engaged with the base portion in the operate mode, the flat front face of the insert portion of the microkeratome blade riding against the flat, rearward face of the partition wall and thereby determine how far the microkeratome blade extends into the base slot.

14. The microkeratome of claim 13, wherein a plurality of insert portions are provided wherein in each insert portion the flat, rearward face of the partition wall is spaced a different distance from the front of the insert portion to thereby provide for different degrees of extension of the microkeratome blade into the base slot to thereby allow for selection of the thickness of corneal flap cut during the keratectomy.

15. The microkeratome of claim 13, wherein the handpiece tip engagement means on the back of the blade insert comprises a vertically oriented slot.

16. The microkeratome of claims 13, wherein at least one of the alignment apertures formed in the head portion and the insert portion has first engagement means adapted to engage with a front portion of a microkeratome handpiece.

17. The microkeratome of claims 16, wherein the first engagement means comprises threads formed in the alignment aperture of the base portion complementary to threads at a front of a microkeratome handpiece, such that when the threads at the front of the microkeratome handpiece are screwed together with the threads of the alignment aperture of the base portion, the insert portion and base portion are locked together, and an oscillating tip of the microkeratome handpiece engages with the handpiece tip engagement means of the microkeratome blade.

18. The microkeratome of claim 1, wherein the vacuum aspiration port extends upwardly from the first guide wall.

19. The microkeratome of claim 1, wherein the microkerotome handpiece comprises a brushless DC motor.

20. The microkeratome of claim 19, wherein the microkerotome handpiece comprises a brushless DC motor.

21. A microkeratome adapted to be used with a microkeratome handpiece with an oscillating tip and a microkeratome blade having a blade portion with a cutting edge and an insert which engages with an aperture formed in the blade portion, the insert having a base which seats on an underside of the blade portion and a riser, the riser having a flat front face and a rear face with a vertical slot formed thereon, the microkeratome being for use in carrying out a keratectomy of a patient's eyeball to create a corneal flap, the microkeratome comprising:

a) a positioning assembly having a platform with an upper surface and a lower surface with a corneal opening formed therethrough, the lower surface comprising a suction ring for application to the surface of the patient's eyeball around the cornea, a vacuum aspiration port in communication with the suction ring, and first and a second spaced apart guide walls extending upwardly from the upper surface of the platform and having curved outer surfaces, and straight parallel inner wall surfaces, the distance from a top of the second guide wall to a bottom surface of the suction ring being at least 3.5 mm to prevent a patient's eyelids from passing over the upper surface of the positioning assembly, the first and second guide walls having horizontal slots formed thereon that extend between ends of the first and second guide walls;

b) a microkeratome head portion comprising a base portion and an insert portion, the base portion comprising a lower planar face with a base slot extending therethrough, a front portion, a rear portion, opposing sides having skates which are slidably engageable with the horizontal slots on the positioning assembly, the slides extending outwardly from the sides and downwardly below the lower planar face of the base portion for slidably engaging the head portion with the positioning assembly such that the lower planar face will slide above the upper surface of the platform of the positioning assembly, and a cavity which communicates with the base slot, the rear portion having an alignment aperture formed therethrough, and the insert portion comprising a blade retention slot for slidably receiving a microkeratome blade, the insert portion fitting within the cavity of the base portion and having a front and a rear, an aperture formed through the rear which aligns with the alignment aperture formed in the base portion when the insert portion is engaged with the base portion in an operation mode; and c) a stop means for preventing the head portion from passing completely through the positioning assembly to thereby leave an uncut section of corneal flap after completing the keratectomy.

22. The microkeratome of claim 21, wherein the ends of the first and second guide walls are beveled in the vicinity of the horizontal slots and the front ends of the skates are beveled, the bevels permitting easy engagement of the microkeratome head portion with the positioning assembly when the positioning assembly is placed on the patient's eyeball.

23. The microkeratome of claim 21, wherein the stop means comprises a first guide wall protrusion on the first guide wall and a protrusions extending from both sides of the insert portion near its rear.

24. The microkeratome of claim 21, wherein the insert portion has a pivot rod at the front which pivotally engages with finger engagement recess on the base portion to permit the insert portion to swung down into the cavity of the base portion in the operation mode, and swung up and completely separated and removed from the base portion without the use of any tools and allows for cleaning and sterilizing between uses of the microkeratome.

25. The microkeratome of claim 21, wherein the blade retention slot in the insert portion is located behind a partition wall, the partition wall having a flat, rearward face located a predetermined distance away from the front of the insert portion and being positioned at an acuate angle relative to the lower planar face of the base portion when the insert portion is engaged with the base portion in the operate mode, the flat front face of the insert portion of the microkeratome blade riding against the flat, rearward face of the partition wall and thereby determining how far the microkeratome blade extends into the base slot.

26. The microkeratome of claims 25, wherein at least one of the alignment apertures formed in the head portion and the insert portion has first engagement means adapted to engage with a front portion of a microkeratome handpiece.

27. The microkeratome of claims 25, wherein the first engagement means comprises threads formed in the alignment aperture of the base portion complementary to threads at a front of a microkeratome handpiece, such that when the threads at the front of the microkeratome handpiece are engaged with the threads of the alignment aperture of the base portion, the insert portion and base portion are locked together, and the oscillating tip of the microkeratome handpiece engages with the vertical slot on the blade insert of the microkeratome blade.

28. A microkeratome adapted to be used with a microkeratome handpiece with an oscillating tip and a microkeratome blade having a blade portion with a cutting edge and an insert which engages with an aperture formed in the blade portion, the insert having a base which seats on an underside of the blade portion and a riser, the riser having a flat front face and a rear face with a vertical slot formed thereon, the microkeratome being for use in carrying out a keratectomy of a patient's eyeball to create a corneal flap, the microkeratome comprising:

a) a positioning assembly having a platform with an upper surface and a lower surface with a corneal opening formed therethrough, the lower surface comprising a suction ring for application to the surface of the patient's eyeball around the cornea, a vacuum aspiration port in communication with the suction ring, and first and a second spaced apart guide walls extending upwardly from the upper surface of the platform and having outer surfaces, and parallel inner surfaces, the guide walls having first sliding engagement means formed on the inner surfaces thereof;

b) a microkeratome head portion comprising a base portion and an insert portion, the base portion comprising a lower planar face with a base slot extending therethrough, a front portion, a rear portion, second sliding engagement which are slidably engageable with the first engagement means on positioning assembly, and a cavity which communicates with the base slot, the rear portion having an alignment aperture formed therethrough, and the insert portion comprising a blade retention slot for slidably receiving a microkeratome blade, the insert portion fitting within the cavity of the base portion and having a front and a rear, an aperture formed through the rear which aligns with the alignment aperture formed in the base portion when the insert portion is engaged with the base portion in an operation mode; and c) a stop means for preventing the head portion from passing completely through the positioning assembly to thereby leave an uncut section of corneal flap after completing the keratectomy.

29. The microkeratome of claims 28, wherein the first and a second spaced apart guide walls are high enough to prevent a patient's eyelids from passing over the upper surface of the positioning assembly.

30. The microkeratome of claims 28, wherein the distance from a top of the second guide wall to a bottom surface of the suction ring being at least 3.5 mm to prevent a patient's eyelids from passing over the upper surface of the positioning assembly.

31. The microkeratome of claim 28, wherein the first sliding engagement means comprises horizontal slots formed on the inner surfaces of the first and second guide walls that extend between ends of the first and second guide walls, and the second sliding engagement means comprise skates which are slidably engageable with the horizontal slots, the slides extending outwardly from the sides and downwardly below the lower planar face of the of the base portion.

32. The microkeratome of claim 31, wherein the ends of the first and second guide walls are beveled in the vicinity of the horizontal slots and the front ends of the skates are beveled, the bevels permitting easy engagement of the microkeratome head portion with the positioning assembly when the positioning assembly is placed on the patient's eyeball.

33. The microkeratome of claim 28, wherein the stop means comprises a first guide wall protrusion on the first guide wall and a protrusions extending from both sides of the insert portion near its rear.

34. The microkeratome of claim 28, wherein the insert portion has a pivot rod at the front which pivotally engages with finger engagement recess on the base portion to permit the insert portion to swung down into the cavity of the base portion in the operation mode, and swung up and completely separated and removed from the base portion without the use of any tools and allows for cleaning and sterilizing between uses of the microkeratome.

35. The microkeratome of claim 28, wherein the blade retention slot in the insert portion is located behind a partition wall, the partition wall having a flat, rearward face located a predetermined distance away from the front of the insert portion and being positioned at an acuate angle relative to the lower planar face of the base portion when the insert portion is engaged with the base portion in the operate mode, the flat front face of the insert portion of the microkeratome blade riding against the flat, rearward face of the partition wall and thereby determining how far the microkeratome blade extends into the base slot.

36. The microkeratome of claims 35, wherein at least one of the alignment apertures formed in the head portion and the insert portion has first engagement means adapted to engage with a front portion of a microkeratome handpiece.

37. The microkeratome of claims 36, wherein the first engagement means comprises threads formed in the alignment aperture of the base portion complementary to threads at a front of a microkeratome handpiece, such that when the threads at the front of the microkeratome handpiece are engaged with the threads of the alignment aperture of the base portion, the insert portion and base portion are locked together, and the oscillating tip of the microkeratome handpiece engages with the vertical slot on the blade insert of the microkeratome blade.

38. The microkeratome of claim 28, wherein the microkerotome handpiece comprises a brushless DC motor.

* * * * *